United States Patent
Aiki et al.

(10) Patent No.: US 11,772,080 B2
(45) Date of Patent: Oct. 3, 2023

(54) CATALYST, METHOD FOR PRODUCING CATALYST, AND METHOD FOR PRODUCING ACRYLONITRILE

(71) Applicant: ASAHI KASEI KABUSHIKI KAISHA, Tokyo (JP)

(72) Inventors: Shota Aiki, Tokyo (JP); Akiyoshi Fukuzawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 96 days.

(21) Appl. No.: 17/436,787

(22) PCT Filed: Mar. 26, 2020

(86) PCT No.: PCT/JP2020/013730
§ 371 (c)(1),
(2) Date: Sep. 7, 2021

(87) PCT Pub. No.: WO2020/213361
PCT Pub. Date: Oct. 22, 2020

(65) Prior Publication Data
US 2022/0168711 A1 Jun. 2, 2022

(30) Foreign Application Priority Data
Apr. 15, 2019 (JP) .................... 2019-077367

(51) Int. Cl.
*B01J 23/883* (2006.01)
*B01J 6/00* (2006.01)
(Continued)

(52) U.S. Cl.
CPC ............ *B01J 23/883* (2013.01); *B01J 6/001* (2013.01); *B01J 35/1014* (2013.01);
(Continued)

(58) Field of Classification Search
CPC ...... B01J 23/883; B01J 6/001; B01J 35/1014; B01J 37/0045; B01J 37/16; B01J 35/0073;
(Continued)

(56) References Cited

U.S. PATENT DOCUMENTS 4,335,264 A * 6/1982 Yates .................... C07C 45/35
568/478
4,425,255 A 1/1984 Toyoda et al.
(Continued)

FOREIGN PATENT DOCUMENTS

CN 109070070 A 12/2018
EP 0 573 713 B1 12/1993
(Continued)

OTHER PUBLICATIONS

International Preliminary Report on Patentability and Written Opinion of the International Searching Authority for International Application No. PCT/JP2020/013730, dated Oct. 28, 2021, with English translation of the Written Opinion.
(Continued)

*Primary Examiner* — Patricia L. Hailey
(74) *Attorney, Agent, or Firm* — Birch, Stewart, Kolasch & Birch, LLP

(57) ABSTRACT

A catalyst comprising molybdenum, bismuth, iron, and nickel, wherein a proportion of a surface concentration of the nickel to a bulk concentration of the nickel is 0.60 to 1.20.

17 Claims, 1 Drawing Sheet

(51) Int. Cl.
*B01J 35/10* (2006.01)
*B01J 37/00* (2006.01)
*B01J 37/16* (2006.01)
*C07C 253/18* (2006.01)

(52) U.S. Cl.
CPC .......... *B01J 37/0045* (2013.01); *B01J 37/16* (2013.01); *C07C 253/18* (2013.01); *C07C 2523/882* (2013.01)

(58) Field of Classification Search
CPC .............. C07C 253/18; C07C 2523/882; C01P 2006/90; C01P 2002/85; C01P 2004/03
USPC .................................. 502/321, 311, 315, 316
See application file for complete search history.

(56) References Cited

U.S. PATENT DOCUMENTS

| | | | |
|---|---|---|---|
| 5,169,822 A * | 12/1992 | Weissman ............... | C10G 45/08 502/313 |
| 6,924,387 B1 | 8/2005 | Chang et al. | |
| 2006/0199730 A1 | 1/2006 | Seely et al. | |
| 2006/0194693 A1 | 8/2006 | Watanabe et al. | |
| 2014/0066298 A1 * | 3/2014 | Han ....................... | B01J 27/049 502/220 |
| 2019/0001309 A1 * | 1/2019 | Fukuzawa ............ | B01J 37/0221 |
| 2019/0070591 A1 | 3/2019 | Motomura et al. | |
| 2019/0168191 A1 | 6/2019 | Aiki et al. | |

FOREIGN PATENT DOCUMENTS

| | | |
|---|---|---|
| JP | 57-56044 A | 4/1982 |
| JP | 2001-205090 A | 7/2001 |
| JP | 2002-502699 A | 1/2002 |
| JP | 2004-313992 A | 11/2004 |
| JP | 2015-157241 A | 9/2015 |
| JP | 2015-157243 A | 9/2015 |
| JP | 2019-5701 A | 1/2019 |
| KR | 10-2011-0130130 A | 12/2011 |
| RU | 2 374 218 C2 | 11/2009 |
| WO | WO 2017/069119 A1 | 4/2017 |
| WO | WO 2017/130906 A1 | 8/2017 |
| WO | WO 2018/043007 A1 | 3/2018 |

OTHER PUBLICATIONS

Ilyin, "Scientific Basis for the Preparation of Catalysts. Creative Heritage and the Most Profound Development of the Works of Professor I.P. Kirillov," State Chemical-Technical University, 2008, p. 96 (2 pages total), with English translation.
Mukhlenov et al., "Catalyst Technology," Chemistry, 1989, p. 95 (2 pages total), with partial English translation.
Panchenkov et al., "Chemical Kinetics and Catalysis," Moscow University Publishing House, 1985, p. 374 (3 pages total), with English translation.
Pavlov et al., "Examples and tasks on the course of processes and devices of chemical technology," Leningrad "Chemistry", 1987, pp. 282 (2 pages total), with English translation.
International Search Report, issued in PCT/JP2020/013730, PCT/ISA/210, dated Jun. 23, 2020.
Written Opinion of the International Searching Authority, issued in PCT/JP2020/013730, PCT/ISA/237, dated Jun. 23, 2020.
Supplementary European Search Report for European Application No. 20792163.6, dated May 6, 2022.

* cited by examiner

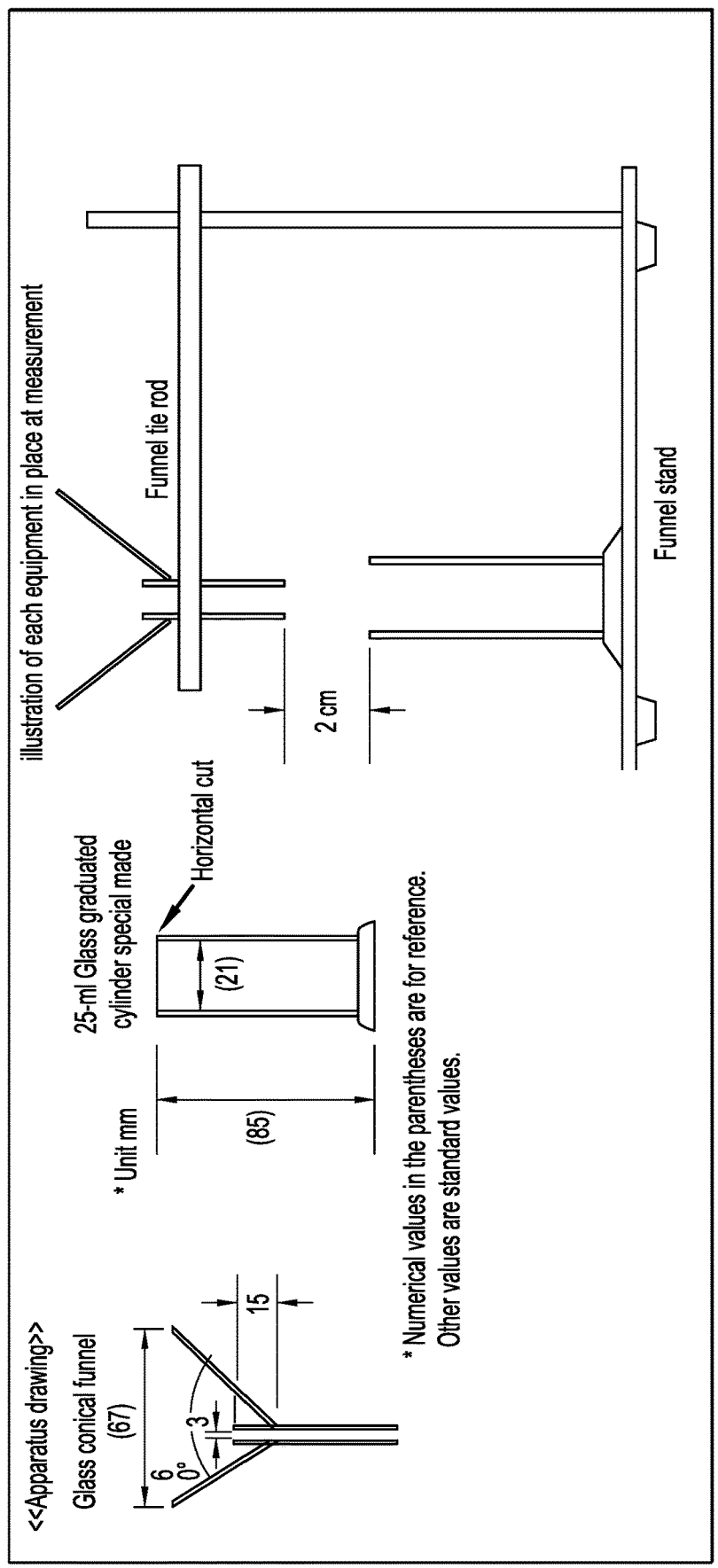

CATALYST, METHOD FOR PRODUCING CATALYST, AND METHOD FOR PRODUCING ACRYLONITRILE

TECHNICAL FIELD

The present invention relates to a catalyst, a method for producing a catalyst, and a method for producing acrylonitrile.

BACKGROUND ART

As a method for producing acrylonitrile, ammoxidation of propylene is known. Additionally, this ammoxidation enables to obtain hydrogen cyanide together with acrylonitrile.

As ammoxidation catalysts, oxide catalysts containing molybdenum, bismuth, and iron and oxide catalysts containing antimony and iron are utilized, and various modifications have been made on the catalysts having these basic compositions for the purpose of enhancing the ammoxidation reaction efficiency.

For example, the fluidized bed catalyst for ammoxidation reaction described in Patent Literature 1 and represented by the following formula (1) can supposedly produce acrylonitrile in a high yield and stably for an extended period of time without requiring to use an excess amount of ammonia in the propylene ammoxidation.

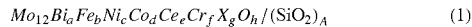

$$Mo_{12}Bi_aFe_bNi_cCo_dCe_eCr_fX_gO_h/(SiO_2)_A \qquad (1)$$

wherein Mo represents molybdenum, Bi represents bismuth, Fe represents iron, Ni represents nickel, Co represents cobalt, Ce represents cerium, Cr represents chromium, X represents at least one element selected from the group consisting of potassium, rubidium, and cesium, $SiO_2$ represents silica, a, b, c, d, e, f, g, and h represent an atomic ratio of each element and satisfy $0.1 \leq a \leq 1$, $1 \leq b \leq 3$, $1 \leq c \leq 6.5$, $1 \leq d \leq 6.5$, $0.2 \leq e \leq 1.2$, $f \leq 0.05$, and $0.05 \leq g \leq 1$, h is an atomic ratio of oxygen atoms that satisfies the valence of each constituent element excluding silica, A represents a silica content (mass %) in the complexes and satisfies $35 \leq A \leq 48$, and the values of $\alpha$, $\beta$, and $\gamma$ calculated from the atomic ratio of each element using the following formulae (2), (3), and (4) satisfy $0.03 \leq \alpha \leq 0.08$, $0.2 \leq \beta \leq 0.4$, and $0.5 \leq \gamma \leq 2$.

$$\alpha = 1.5a/(1.5(b+f)+c+d) \qquad (2)$$

$$\beta = 1.5(b+f)/(c+d) \qquad (3)$$

$$\gamma = d/c \qquad (4)$$

CITATION LIST

Patent Literature

Patent Literature 1
International Publication No. WO 2017/130906

SUMMARY OF INVENTION

Technical Problem

The propylene ammoxidation is expected to increase the productivity of hydrogen cyanide together with acrylonitrile, and accordingly the enhancement in the hydrogen cyanide yield while maintaining a high yield of acrylonitrile has been a challenge.

The present invention has been made in light of the above problem and has an object to provide a catalyst capable of enhancing a hydrogen cyanide yield while maintaining a high yield of acrylonitrile in the propylene ammoxidation.

Solution to Problem

The present inventors conducted extensive studies to solve the above problem and consequently found that the above problem can be solved by using a catalyst containing specific metal species and having a proportion of a surface concentration of the nickel to a bulk concentration of the nickel within a specific range, whereby the present invention was accomplished.

That is, the present invention is as follows.

[1]
A catalyst comprising molybdenum, bismuth, iron, and nickel,
wherein a proportion of a surface concentration of the nickel to a bulk concentration of the nickel is 0.60 to 1.20.

[2]
The catalyst according to [1], wherein a proportion of the surface concentration of the nickel to a surface concentration of the molybdenum is 0.15 to 0.40.

[3]
The catalyst according to [1] or [2], further comprising cobalt,
wherein a proportion of a surface concentration of the cobalt to a bulk concentration of the cobalt is 0.80 to 1.40.

[4]
The catalyst according to any one of [1] to [3], further comprising cobalt,
wherein a proportion of a surface concentration of the cobalt to a surface concentration of the molybdenum is 0.15 to 0.40.

[5]
The catalyst according to any one of [1] to [4], having a specific surface area of 10 to 70 m²/g.

[6]
The catalyst according to any one of [1] to [5], wherein a proportion of particles having a particle size of 45 μm or less in a volume-based particle size distribution is 5 to 45%.

[7]
The catalyst according to any one of [1] to [6], having a median diameter of 10 to 180 μm.

[8]
The catalyst according to any one of [1] to [7], having an apparent specific gravity of 0.8 to 1.2 g/cc.

[9]
The catalyst according to any one of [1] to [8], comprising a metal oxide having a composition represented by the following formula (1):

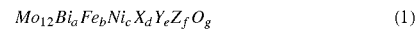

$$Mo_{12}Bi_aFe_bNi_cX_dY_eZ_fO_g \qquad (1)$$

wherein,
X represents one or more elements selected from the group consisting of cobalt, magnesium, calcium, zinc, strontium, barium, and tungsten,
Y represents one or more elements selected from the group consisting of cerium, chromium, lanthanum, neodymium, yttrium, praseodymium, samarium, aluminum, boron, gallium, and indium, Z represents one or more elements selected from the group consisting of sodium, potassium, rubidium, and cesium, a, b, c, d, e, and f satisfy $0.1 \leq a \leq 2.0$, $0.1 \leq b \leq 3.0$, $0.1 \leq c \leq 10.0$, $0 \leq d \leq 10.0$, $0.1 \leq e \leq 3.0$, and $0.01 \leq f \leq 2.0$, respectively, and g is number of oxygen atoms required to satisfy valence requirements of other elements present.

[10]

The catalyst according to any one of [1] to [9], further comprising a silica-containing carrier.

[11]

The catalyst according to any one of [1] to [10] for use in ammoxidation.

[12]

A method for producing the catalyst according to any one of [1] to [11], comprising:

a step of spray drying a slurry containing molybdenum, bismuth, iron, and nickel to obtain dried parties, and calcining the dried particles in the air to obtain calcined particles, and a step of reducing the calcined particles in the presence of a reducing gas and oxygen.

[13]

The method for producing the catalyst according to [12], wherein molybdenum is further added in the step of reduction in the presence of a reducing gas and oxygen.

[14]

A method for producing acrylonitrile, comprising a step of reacting propylene, molecular oxygen, and ammonia in the presence of the catalyst according to any one of [1] to [11].

Advantageous Effects of Invention

According to the present invention, a catalyst capable of enhancing a hydrogen cyanide yield while maintaining a high yield of acrylonitrile, which is the product of the propylene ammoxidation, can be provided. Thus, a production method including a step of ammoxidating propylene in the presence of the catalyst of the present invention can increase the productivity of acrylonitrile and hydrogen cyanide and efficiently supply acrylonitrile and hydrogen cyanide.

Hydrogen cyanide is a compound commonly utilized in industry as a starting material for chemical products such as sodium cyanide. Hydrogen cyanide can be produced using a platinum catalyst and methane and ammonia as starting materials. However, this technique needs to have a reaction temperature of almost 900° C. and is thus a reaction with a significant energy loss. Meanwhile, hydrogen cyanide can also be produced as a by-product of the propylene ammoxidation reaction. The reaction, in this case, can be carried out at a comparatively low temperature of 400 to 500° C. and thus decreases the energy loss. For this reason, the enhancement in the hydrogen cyanide yield in the propylene ammoxidation reaction is useful from the industrial and environmental viewpoints.

BRIEF DESCRIPTION OF DRAWING

FIG. 1 shows a schematic view to explain a method for measuring an apparent specific gravity of the catalyst.

DESCRIPTION OF EMBODIMENTS

Hereinafter, embodiments of the present invention will be described in detail (hereinafter, referred to as the "present embodiment"). The present invention is not limited to the following present embodiments and can be carried out in various modifications within the range of subject matter. In the present description, the expression of "to" between numerical values or physical property values means to include those values before and after the "to". For example, a notation for a numerical value range represented as "1 to 100" includes both of "100" as the upper limit value and "1" as the lower limit value thereof. Similarly, the same applies to other notations for numerical value ranges.

The catalyst of the present embodiment can contain molybdenum, bismuth, iron, and nickel and also contain cobalt and other elements as needed. Further, the catalyst of the present embodiment has a proportion of a surface concentration of the nickel to a bulk concentration of the nickel of 0.60 to 1.20. The catalyst of the present embodiment, when used for the propylene ammoxidation, can enhance a hydrogen cyanide yield while maintaining a high yield of acrylonitrile. An aspect of the catalyst of the present embodiment is the catalyst for use in the ammoxidation.

The proportion of the surface concentration of the nickel to the bulk concentration of the nickel (surface Ni concentration/bulk Ni concentration ratio) of the catalyst of the present embodiment is 0.60 to 1.20, preferably 0.70 to 1.20, and more preferably 0.80 to 1.15. The "bulk concentration of the nickel" used in the present embodiment is a value calculated from an element composition of feed starting materials when preparing the catalyst and is the nickel concentration determined supposing that throughout the entire catalyst is homogeneous. Additionally, the "surface concentration of the nickel" used in the present embodiment is the nickel concentration determined by analyzing a metal composition of the catalyst surface (the surface of catalyst particles). The surface concentration of the nickel to the bulk concentration of the nickel can be specifically measured by the method described in Example.

When the proportion of the surface concentration of the nickel to the bulk concentration of the nickel is 0.60 to 1.20, a hydrogen cyanide yield can be enhanced while maintaining a high yield of acrylonitrile in the propylene ammoxidation.

Examples of the method for adjusting the proportion of the surface concentration of the nickel to the bulk concentration of the nickel to 0.60 to 1.20 include, as described in the method for producing catalyst to be described later, a method in which reduction treatment is carried out when preparing the catalyst and oxygen is controlled to be in a deficient state in the system of this reduction treatment.

The proportion of the surface concentration of the nickel to the surface concentration of the molybdenum (surface Ni concentration/surface Mo concentration ratio) of the catalyst of the present embodiment is not particularly limited but preferably 0.15 to 0.40. When the proportion of the surface concentration of the nickel to the surface concentration of the molybdenum is 0.15 to 0.40, a hydrogen cyanide yield can be enhanced while maintaining a high yield of acrylonitrile in the propylene ammoxidation.

When the catalyst of the present embodiment contains cobalt, the proportion of a surface concentration of the cobalt to a bulk concentration of the cobalt (surface Co concentration/bulk Co concentration ratio) is not particularly limited but preferably 0.80 to 1.40. When the proportion of the surface concentration of the cobalt to a bulk concentration of the cobalt is 0.80 to 1.40, a hydrogen cyanide yield can be enhanced while maintaining a high yield of acrylonitrile in the propylene ammoxidation.

When the catalyst of the present embodiment contains cobalt, the proportion of the surface concentration of the cobalt to the surface concentration of the molybdenum (surface Co concentration/surface Mo concentration ratio) is not particularly limited but preferably 0.15 to 0.40. When the proportion of the surface concentration of the cobalt to the surface concentration of the molybdenum is 0.15 to 0.40, a hydrogen cyanide yield can be enhanced while maintaining a high yield of acrylonitrile in the propylene ammoxidation.

The complex oxide of cobalt or nickel and molybdenum serves to decompose acrylonitrile and produce hydrogen cyanide. An increased concentration of these oxides of the catalyst surface can efficiently enhance a hydrogen cyanide yield.

The catalyst of the present embodiment is not particularly limited as long as it contains at least molybdenum (Mo), bismuth (Bi), iron (Fe) and nickel (Ni) and can also contain other elements. Examples of other elements include cobalt, magnesium, alkali metals and the like. For example, the catalyst containing magnesium can stabilize the crystal phase and tends to decrease the transformation of the crystal phase to the a type, which leads to performance decline when subjected to the fluidized bed reaction. The catalyst containing an alkali metal tends to decrease the production of by-products and keep a calcination temperature of the catalyst within a preferable zone.

The catalyst of the present embodiment preferably contains a metal oxide having the composition represented by the formula (1).

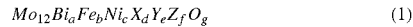

$$Mo_{12}Bi_aFe_bNi_cX_dY_eZ_fO_g \qquad (1)$$

wherein

X represents one or more elements selected from the group consisting of cobalt, magnesium, calcium, zinc, strontium, barium, and tungsten, Y represents one or more elements selected from the group consisting of cerium, chromium, lanthanum, neodymium, yttrium, praseodymium, samarium, aluminum, boron, gallium, and indium, Z represents one or more elements selected from the group consisting of sodium, potassium, rubidium, and cesium, a, b, c, d, e, and f satisfy $0.1 \le a \le 2.0$, $0.1 \le b \le 3.0$, $0.1 \le c \le 10.0$, $0 \le d \le 10.0$, $0.1 \le e \le 3.0$, and $0.01 \le f \le 2.0$, respectively, and g is the number of oxygen atoms required to satisfy valence requirements of other elements present.

The atomic ratio a of bismuth to 12 atoms of molybdenum is $0.1 \le a \le 2.0$, and preferably $0.2 \le a \le 1.8$. When a is 0.1 or more and 2.0 or less, the yield at the initial reaction for producing acrylonitrile and hydrogen cyanide tends to be higher, and the reaction stability tends to be excellent.

The atomic ratio b of iron to 12 atoms of molybdenum is $0.1 \le b \le 3.0$, and preferably $0.2 \le b \le 2.6$.

The atomic ratio c of nickel to 12 atoms of molybdenum is $0.1 \le c \le 10.0$, and preferably $0.2 \le c \le 9.6$.

The atomic ratio d of the element X to 12 atoms of molybdenum is $0 \le d \le 10.0$, and preferably $0.2 \le d \le 9.6$. The element X is one or more selected from the group consisting of cobalt, magnesium, calcium, zinc, strontium, barium, and tungsten.

The atomic ratio e of the element Y to 12 atoms of molybdenum is $0.1 \le e \le 3.0$, and preferably $0.2 \le e \le 2.8$. The element Y is one or more selected from the group consisting of cerium, chromium, lanthanum, neodymium, yttrium, praseodymium, samarium, aluminum, boron, gallium, and indium. The element Y preferably includes at least cerium and can also further include one or more elements selected from the group consisting of chromium, lanthanum, neodymium, yttrium, praseodymium, samarium, aluminum, gallium, and indium.

The atomic ratio f of the element Z to 12 atoms of molybdenum is $0.01 \le f \le 2.0$, and preferably $0.03 \le f \le 1.8$. The element Z is one or more selected from the group consisting of sodium, potassium, rubidium, and cesium.

The atomic ratio g of oxygen to 12 atoms of molybdenum is the number of oxygen atoms required to satisfy valence requirements of other elements present.

The catalyst of the present embodiment can also be those in which the above metal oxide is supported on a carrier. That is, the catalyst of the present embodiment can be a catalyst including the above metal oxide and a carrier. As the carrier, oxides such as silica, alumina, titania, and zirconia are used, and silica is preferable from viewpoints of low object selectivity decrease, and good abrasion resistance and particle strength of the formed catalyst particles. That is, one of the preferable aspects of the catalyst of the present embodiment is a catalyst further including a silica-containing carrier.

The amount of the silica carrier used with respect to the total mass of the silica carrier and a complex metal oxide ranges from 20 mass % to 80 mass %, preferably 30 mass % to 70 mass %, and further preferably 40 mass % to 60 mass %.

The specific surface area of the catalyst of the present embodiment is not particularly limited but preferably 10 to 70 m$^2$/g. The specific surface area of the catalyst of the present embodiment can be measured by preliminarily drying a sample in a helium circulation at 300° C. for 15 minutes using a Micromeritics automatic specific surface area analyzer Gemini V by the BET one-point method using nitrogen as an adsorption gas.

The proportion of particles having a particle size of 45 μm or less in the volume-based particle size distribution of the catalyst of the present embodiment is not particularly limited but preferably 5 to 45% (accumulation of 45 μm in the volume-based distribution is 5 to 45%). The proportion of particles having a particle size of 45 μm or less (accumulation of 45 μm in the volume-based distribution) can be obtained from the volume-based particle size obtained by adding 0.6 g of the catalyst to 250 ml of water as dispersion medium, performing ultrasonic dispersion for 1 minute and then measuring using a laser diffraction/scattering particle size distribution analyzer LA-300, manufactured by HORIBA, Ltd., under a condition of a relative refractive index of 1.40.

The shape of the catalyst of the present embodiment is not particularly limited but, when used as a fluidized bed catalyst, preferably spherical from a viewpoint of fluidity. The median diameter of the catalyst of the present embodiment is not particularly limited but preferably 10 to 180 μm, and more preferably 20 to 150 μm. The median diameter of the catalyst of the present invention can be obtained by adding 0.6 g of the catalyst to 250 ml of water as dispersion medium, performing ultrasonic dispersion for 1 minute and then measuring using a laser diffraction/scattering particle size distribution analyzer LA-300, manufactured by HORIBA, Ltd., under a condition of a relative refractive index of 1.40.

The apparent specific gravity of the catalyst of the present embodiment is not particularly limited but preferably 0.8 to 1.2 g/cc. FIG. 1 is a schematic view showing a method for measuring an apparent specific gravity of the catalyst of the present embodiment. Using a funnel and a graduated cylinder shown in FIG. 1, the catalyst is allowed to drop from the funnel to the graduated cylinder, the catalyst at the upper part of the graduated cylinder is wiped off using a metallic ruler or the like, the graduated cylinder is weighed, and a weight of the tared graduated cylinder is subtracted whereby a weight of the catalyst is obtained. An apparent specific gravity can be calculated by the following formula using the obtained catalyst weight.

Apparent specific gravity=weight of catalyst (g)/25 (cc)

[Method for Producing the Catalyst]

The catalyst of the present embodiment is produced by a production method including a step of spray drying a slurry containing molybdenum, bismuth, iron, and nickel to obtain dried parties, and calcining the dried particles in the air to obtain calcined particles (hereinafter, also referred to as Step I") and a step of reducing the calcined particles in the presence of a reducing gas and oxygen (hereinafter, also referred to as Step II").

(Step I)

Step I in the method for producing the catalyst of the present embodiment is a step of spray drying a slurry containing molybdenum, bismuth, iron, and nickel to obtain dried particles, and calcining the dried particles in the air to obtain calcined particles. The calcined particle is also called a catalyst precursor.

The above calcined particle can be produced by a known method, for example, in reference to the production method described in International Publication No. WO 2018/211858. The above calcined product can also contain metals contained in the composition represented by the formula (1) in addition to molybdenum, bismuth, iron, and nickel. The calcined particle containing molybdenum, bismuth, iron, and nickel is preferably the metal oxide having the composition represented by the formula (1).

The slurry containing molybdenum, bismuth, iron, and nickel can be obtained by mixing starting materials of the catalyst and a solvent. The solvent is preferably water, and the slurry is preferably an aqueous slurry. When the catalyst of the present embodiment is supported on silica, a preparation method of mixing and stirring an aqueous solution containing molybdenum with an aqueous solution containing silica and then mixing and stirring a solution containing bismuth, iron, nickel, and other metals therewith is preferably used.

A silica sol is preferable as a starting material of silica. A preferable concentration of a silica sol in a state of the starting material in which other metal components are not mixed is 10 to 50 mass %.

The starting material of each element constituting the catalyst such as molybdenum, bismuth, cerium, iron, nickel, cobalt, magnesium, zinc, potassium, rubidium, and cesium for preparing the slurry is a salt soluble in water or nitric acid, and examples include an ammonium salt, a nitrate, a hydrochloride, a sulfate, and an organic acid salt of each metal. An ammonium salt is preferably used as the starting material containing molybdenum, and a nitrate is preferably used as the starting material containing bismuth, cerium, iron, nickel, magnesium, zinc, potassium, rubidium, and cesium.

The slurry containing molybdenum, bismuth, iron, and nickel is spray dried to thereby prepare dried particles. In the spray drying, the slurry is spray dried whereby spherical particles are obtained. The spraying of aqueous slurry can be carried out by typically used industrial centrifugal method, two-fluid nozzle method, and high pressure nozzle method, and the spraying is preferably carried out by the centrifugal method. For drying, a heated air is preferably used, and examples of the heat source for drying include steam and an electric heater. The inlet temperature of a dryer is preferably 100° C. to 400° C., and more preferably 150° C. to 300° C. The outlet temperature of a dryer is preferably 100° C. to 180° C., and more preferably 120° C. to 170° C.

The dried particles obtained as described above are calcined in the air to obtain calcined particles. The calcination is carried out in a typical tunnel or rotary kiln. The calcination temperature ranges preferably 500 to 750° C., and more preferably 500 to 680° C. The calcination time can be suitably adjusted according to a calcination temperature and ranges preferably 1 to 20 hours.

The shape of calcined particle is not particularly limited but preferably spherical. The median diameter of calcined particle is not particularly limited but preferably 10 to 180 μm. The median diameter of the calcined particles can be obtained by adding 0.6 g of the calcined particles to 250 ml of water as dispersion medium, performing ultrasonic dispersion for 1 minute and then measuring using a laser diffraction/scattering particle size distribution analyzer LA-300, manufactured by HORIBA, Ltd., under a condition of a relative refractive index of 1.40.

(Step II)

Step II in the method for producing the catalyst of the present embodiment is a step of reducing the calcined particles obtained in Step I in the presence of a reducing gas and oxygen. Step II can be preferably carried out using a fluidized bed reactor as the reactor. The fluidized bed reactor is not particularly limited, and a preferably used is a vertical cylindrical reactor equipped with an air distributor, a starting material gas dispersion pipe for supplying propylene and ammonia thereon, and a reactor outlet.

The calcined particles obtained by Step I are filled in the reactor, and as needed, first preferably subjected to a state where the particles are contacted with a mixed gas containing propylene, ammonia, oxygen, and helium. In the present description, the treatment of subjecting to such a state is also called the reduction pretreatment.

In the present description, the oxygen refers to molecular oxygen, and the oxygen source is the air. In the present invention, the oxygen concentration control is important, and a molar ratio is sometimes presented in terms of the oxygen, not the air, to simplify descriptions, but an air content is controlled in such a way as to be desired number of oxygen moles and molar ratio. Given that an oxygen concentration in the air is 21%, an oxygen molar ratio is convertible using the following formula.

Oxygen molar ratio=air molar ratio×0.21

The contact time of this mixed gas and the calcined particles is not particularly limited but typically 0.5 to 30 seconds, and preferably 1 to 10 seconds. The contact time herein is a contact time determined by the method described in Example. The temperature of reduction pretreatment is preferably 400 to 500° C., and more preferably 420 to 480° C. During the pretreatment, the molar ratio of ammonia/propylene in the mixed gas is preferably set to be 1.0 to 5.0. Additionally, the molar ratio of oxygen/propylene is preferably set so that an oxygen concentration to be detected at the reactor outlet (hereinafter, also referred to as the oxygen concentration in the reactor outlet gas) is 0.18 to 0.22 vol %. At this time, the propylene conversion rate is preferably 98% or more, and more preferably 99% or more.

In the method for producing the catalyst of the present embodiment, a molybdenum compound can be added. The addition of a molybdenum compound enhances the catalyst activity for ammonia and is likely to increase an acrylonitrile yield. A molybdenum compound is preferably added to the calcined particles obtained in Step I in the step of reducing the calcined particles obtained in Step I in the presence of a reducing gas and oxygen, or to the calcined particles obtained in Step I in the above reduction pretreatment, with adding to the calcined particles obtained in Step I in the above reduction pretreatment being more preferable. The molybdenum compound addition preferably uses ammonium salts of molybdenum.

The amount of a molybdenum compound to be added is, assuming that an amount of substance of molybdenum contained in the calcined particles obtained in Step I is 12 and based on the value of this amount of substance (amount of substance 12), preferably an amount equivalent to 0.05 to 3.0, and more preferably an amount equivalent to 0.1 to 1.0.

In the method for producing the catalyst of the present embodiment, the reduction treatment is preferably carried out by controlling oxygen to be in a deficient state in the reactor. Examples of the specific method of reduction treatment include a method of decreasing an oxygen content in the reactor by adjusting an oxygen/propylene molar ratio. A significantly decreased oxygen/propylene molar ratio controls a ratio of surface nickel concentration/bulk nickel concentration to be a high value.

The decreased oxygen content can be confirmed by detecting an oxygen concentration in the reactor outlet gas. The oxygen having been in a deficient state in the reactor by significantly decreasing the oxygen/propylene molar ratio can be confirmed by the measurement of an oxygen concentration in the reactor outlet gas being 0 vol %. For this reason, it is preferable to control an oxygen flow rate into the reactor be decreased or the like in such a way that an oxygen concentration in the reactor outlet gas is 0 vol %. The oxygen having been in a deficient state in the reactor can also be confirmed by a propylene conversion rate ranging from 89 to 96%. A more preferable oxygen deficient state in the reactor can be confirmed by a propylene conversion rate ranging from 90 to 95%.

The duration of an oxygen deficient state in the reactor is preferably 10 minutes to less than 5 hours, and more preferably 30 minutes to 2 hours. When an oxygen concentration and such a duration are within the above ranges, a ratio of surface nickel concentration/bulk nickel concentration tends to be controlled to be 0.60 to 1.20, thereby likely obtaining the catalyst capable of enhancing a hydrogen cyanide yield while maintaining a high yield of acrylonitrile, which is the product of the propylene ammoxidation.

The molar ratio of an oxygen/propylene in the reduction treatment is specifically preferably decreased by 0.10 or more and 0.50 or less, and more preferably 0.20 or more and 0.40 or less, from the molar ratio of oxygen/propylene in the reduction pretreatment.

The molar ratio of oxygen/propylene in the reduction pretreatment herein is specified based on an oxygen flow rate and a propylene flow rate to the reactor when an oxygen concentration in the reactor outlet gas reaches 0.18 to 0.22 vol %.

The decrease of 0.10 or more in the molar ratio of oxygen/propylene in the reduction treatment from the molar ratio of oxygen/propylene in the reduction pretreatment can sufficiently decrease an oxygen concentration in the reactor, thereby likely obtaining the catalyst capable of enhancing a hydrogen cyanide yield. Further, the decrease of 0.50 or less in the molar ratio of oxygen/propylene in the reduction treatment from the molar ratio of oxygen/propylene in the reduction pretreatment tends to obtain the catalyst capable of maintaining a high yield of acrylonitrile.

The reduction treatment temperature is preferably 400 to 500° C., and more preferably 420 to 480° C.

In Step II, an oxygen concentration can be adjusted after the reduction treatment to increase to the oxygen concentration at the reduction pretreatment to stop the reduction treatment. During this operation, it is preferable that an oxygen concentration be gradually increased to stop the reduction treatment slowly.

The stop of reduction treatment is preferably started by increasing the molar ratio of oxygen/propylene that has been decreased during the reduction treatment. Additionally, the gas conditions of the molar ratio of ammonia/propylene, the molar ratio of oxygen/propylene, and the contact time are preferably adjusted in such a way as to control a sulfuric acid consumption rate to be defined in Example to be 10 to 30 kg/T-AN, an oxygen concentration in the reactor outlet gas to be more than 0 vol %, and a propylene conversion rate to be 97% or more and 100% or less. The above gas conditions are preferably continued for 30 minutes or more and 5 hours or less. The reduction posttreatment temperature is preferably 300 to 500° C., and more preferably 400 to 480° C.

Thereafter, the molar ratio of oxygen/propylene is further preferably adjusted to control an oxygen concentration in the reactor outlet gas to be the oxygen concentration at the reduction pretreatment.

[Method for Producing Acrylonitrile and Hydrogen Cyanide]

The method for producing acrylonitrile of the present embodiment uses the catalyst of the present embodiment. That is, the method for producing acrylonitrile of the present embodiment includes a step of reacting propylene, oxygen, and ammonia in the presence of the catalyst of the present embodiment. The production method of the present embodiment is preferably carried out by the fluidized bed ammoxidation reaction. The acrylonitrile production of the present embodiment can be carried out using the same reactor as the fluidized bed reactor used for producing the catalyst described above. The production method of the present embodiment can produce acrylonitrile and hydrogen cyanide.

The method for producing acrylonitrile of the present embodiment can also be carried out, for example, in the typically used fluidized bed reactor. The starting materials, propylene and ammonia, do not necessarily need to be in high purity and those of industrial grades can be used. Further, it is typically preferable to use the air as the molecular oxygen source, but a gas having an increased oxygen concentration by mixing oxygen with the air can also be used.

When an oxygen source is the air in the method for producing acrylonitrile of the present embodiment, the composition of starting material gases (molar ratio of ammonia and air to propylene; propylene/ammonia/air) ranges preferably 1/(0.8 to 2.5)/(7.0 to 12.0), and more preferably 1/(0.9 to 1.3)/(8.0 to 11.0).

The reaction temperature in the method for producing acrylonitrile of the present embodiment ranges preferably from 300 to 500° C., and more preferably from 400 to 480° C. The reaction pressure ranges preferably from atmospheric pressure to 0.3 MPa. The contact time of the starting material gases and the catalyst is preferably 0.5 to 20 (sec·g/cc), and more preferably 1 to 10 (sec·g/cc).

EXAMPLES

Hereinafter, the present embodiment is more specifically described in reference to the examples but is not at all limited to these examples. The evaluation methods for various physical properties are as described below.
[Proportion of a Surface Concentration of the Nickel to a Bulk Concentration of the Nickel]

The bulk concentration of the nickel was calculated from an element composition of feed starting materials when preparing the catalyst and determined supposing that throughout the entire catalyst is homogeneous. Specifically, with the elements excluding oxygen constituting the catalyst being 100%, the weight concentration of nickel was defined as the bulk concentration of the nickel. The elements excluding oxygen constituting the catalyst includes, for example, elements excluding oxygen in the carrier such as silicone in $SiO_2$.

The "surface concentration of the nickel" is a weight concentration of nickel obtained by measuring the catalyst surface by the energy dispersive X-ray spectrometry (EDX) using a scanning electron microscopy (SEM) and when a weight of the elements excluding oxygen constituting the catalyst is 100%. The specific measurement method is described below.

For pretreating a sample, a 10 mm-square carbon tape was attached on a φ15-mm carbon sample support, and catalyst particles were spread all over thereon and fixed. Then, the surface of catalyst particles was coated with osmium tetraoxide to form a metal osmium layer, which was electrically conducted and measured. For the osmium tetraoxide coating, 1 g of osmium acid (manufactured by Nisshin EM Co., Ltd.) was used as the osmium tetraoxide source, an osmium coater HPC-1SW manufactured by Vacuum Device was used, and the coating time was 5 seconds. According to the catalog of an osmium coater HPC-1SW, a 1.5 nm-metal osmium layer was presumably formed on the catalyst particle surface.

For SEM, Hitachi SU-70 equipped with a schottky-type electron gun was used. For the EDX detector, a Horiba EMAX X-max was used. The accelerating voltage of SEM was set to be 10 kV, and the working distance from an objective lens was 15 mm. The EDX analysis area was a 2 mm×2 mm square, which was made to be a large area in which 500 or more particles were observed so that the impact on composition inconsistency among particles was decreased. K line was used for the quantitative determination of Ni. The Ni—K line intensity was weak under the accelerating voltage of the present condition, and thus the spectrum acquisition time was 300 seconds. For the quantitative determinations of the elements excluding Ni constituting the catalyst, the following exciting lines were used; Co—K line, Mg—K line, Si—K line, Fe—K line, Mo—L line, Ce—L line, Bi—M line, and Cr—K line.

Peak intensities were obtained in terms of peak integrated areas, and the elements excluding oxygen constituting the catalyst were subjected to the XPP method using a measurement software installed in the above EDX detector to determine quantitative values of the elements. The X line intensity of each element used for the quantitative calculation was determined by removing continuous X-ray components and further carrying out peak resolution when peaks overlapped. Trace alkali metals such as Rb and K were not quantitatively determinable and hence excluded from the calculation. The XPP method was referred to the literature, Quantitative Analysis of Homogeneous or Stratified Microvolumes Applying the Model "PAP" Electron Probe Quantitation pp 31-75 Jean-Louis PouchouFrancoise Pichoir (1991). The proportion of the surface concentration of the nickel to the bulk concentration of the nickel was obtained from the surface nickel concentration/bulk nickel concentration.

The proportion of the surface concentration of the nickel to the surface concentration of the molybdenum was obtained in the same manner as the above calculation method of the proportion of the surface concentration of the nickel to the bulk concentration of the nickel. Similarly, the proportion of the surface concentration of the cobalt to the bulk concentration of the cobalt was obtained. Further, the proportion of the surface concentration of the cobalt to the surface concentration of the molybdenum was similarly obtained.
[Propylene Conversion Rate, Acrylonitrile Yield, Hydrogen Cyanide Yield]

Using the catalyst obtained in Examples and Comparative Examples, acrylonitrile and hydrogen cyanide were produced by the propylene ammoxidation reaction. For the reaction tube used during the reaction, a Pyrex (registered trademark) glass tube with 16 built-in 10-mesh wire meshes at 1 cm interval and having an inner diameter of 25 mm was used.

With a catalyst amount of 50 cc, a reaction temperature of 430° C., and a reaction pressure of 0.17 MPa being preset, a mixed gas of propylene/ammonia/air was supplied at 250 to 450 cc/sec (in terms of NTP) as the total gas flow rate to carry out the reaction. During this operation, the propylene content in the mixed gas was 9 vol % and the molar ratio of propylene/ammonia/air was 1/(0.7 to 2.5)/(8.0 to 13.5), and within which ranges, an ammonia flow rate was suitably changed so that a sulfuric acid consumption rate defined by the following formula was 20±2 kg/T-AN, and an air flow rate was suitably changed so that an oxygen concentration in the reactor outlet gas was 0.2±0.02 vol %. Further, the flow velocity of the entire mixed gas was changed to change the contact time defined by the following formula and set so that the propylene conversion rate defined by the following formula was 99.3±0.2%.

The acrylonitrile yield and the hydrogen cyanide yield produced by the reaction were the values defined as the following formulae. The amount of substance of the product was defined based on the number of carbon atoms of propylene, which is the starting material.

$$\text{Sulfuric acid consumption rate (kg}/T\text{-}AN) = \frac{\text{Weight of sulfuric acid required to neutralize unreacted ammonia (kg)}}{\text{Production weight of acrylonitrile }(T)}$$

$$\text{Contact time (sec.)} = \frac{\text{Catalyst amount (cc)}}{\text{Mixed gas flow rate (cc-}NTP/\text{sec.)}} \times \frac{273}{273 + \text{reaction temperature (°C.)}} \times \frac{\text{Reaction pressure (MPa)}}{0.10}$$

$$\text{Propylene conversion rate (\%)} = \frac{\text{Consumed propylene (mol)}}{\text{Supplied propylene (mol)}} \times 100$$

$$\text{Acylonitrile yield (\%)} = \frac{\text{Produced acrylonitrile (mol)}/}{\text{Supplied propylene (mol)}} \times 100$$

$$\text{Hydrogene cyanide yield (\%)} = \frac{\text{Produced hydrogen cyanide (mol)}}{\text{Supplied propylene (mol)}} \times 100$$

Example 1

(Preparation of Catalyst Precursor)

Produced first by the following procedure was a catalyst in which 60 mass % of a metal oxide, which was produced by adjusting feed masses of the starting materials in such a way that the composition thereof was $Mo_{12}Bi_{0.40}Fe_{1.70}Ni_{5.30}Mg_{2.10}Ce_{0.80}Rb_{0.11}O_g$, was supported on 40 mass % of silica ($SiO_2$).

666.7 g of an aqueous silica sol containing 30 mass % of $SiO_2$ having an average particle size of primary particles of 12 nm and 666.7 g of an aqueous silica sol containing 30 mass % of $SiO_2$ having an average particle size of primary particles of 41 nm were mixed to obtain a mixed solution of 2 kinds of silica.

25.0 g of an oxalic acid dihydrate dissolved in 200 g of water was then added to the above silica mixed solution.

Subsequently, a solution in which 493 g of ammonium paramolybdate $[(NH_4)_6MO_7O_{24}\cdot 4H_2O]$ was dissolved in 886 g of water was added to the mixed solution of the above silica sols and oxalic acid.

Then, a solution obtained by dissolving 45.2 g of bismuth nitrate $[Bi(NO_3)_3\cdot 5H_2O]$, 160 g of iron nitrate $[Fe(NO_3)_3\cdot 9H_2O]$, 359 g of nickel nitrate $[Ni(NO_3)_2\cdot 6H_2O]$, 80.8 g of cerium nitrate $[Ce(NO_3)_3\cdot 6H_2O]$, and 3.78 g of rubidium nitrate $[RbNO_3]$ in 399 g of a nitric acid solution having a 16.6 mass % concentration was added to the above mixed solution to obtain an aqueous starting material mixture (starting material slurry). Then, using a sprayer equipped with a disc rotor installed at the center of the upper part of a dryer, the above aqueous starting material mixture was spray dried under the conditions of an inlet temperature of about 230° C. and an outlet temperature of about 110° C. The number of disc rotation was set to be 12500 rotations/min. The obtained dried product was retained at 200° C. for 5 minutes, the temperature was increased from 200° C. to 450° C. at 2.5° C./min, and the dried product was retained at 450° C. for 20 minutes and thereby denitrated. The obtained denitrated powder was calcined at 580° C. for 2 hours to obtain the catalyst precursor.

(Reduction Treatment)

(1) Reduction Pretreatment

Further, using a Pyrex (registered trademark) glass tube with 16 built-in 10-mesh wire meshes at 1 cm interval and having an inner diameter of 25 mm, 0.82 g of ammonium paramolybdate $[(NH_4)_6MO_7O_{24}\cdot 4H_2O]$ (equivalent to 0.4 on a basis of molybdenum 12) was mixed with 50 cc of the catalyst precursor, and with a temperature of 460° C. and a pressure of 0.17 MPa being set, a mixed gas (propylene, ammonia, oxygen, helium) having 9 vol % of propylene was allowed to pass therethrough. The gas flow rate was set so that the contact time defined by the following formula was 3.5 seconds. The molar ratio of ammonia/propylene was set to be 1.7, and the oxygen/propylene molar ratio was set so that the oxygen concentration in the reactor outlet gas was 0.2±0.02 vol %.

(2) Reduction Treatment

After setting the gas conditions as described above, an operation was performed to decrease the oxygen/propylene molar ratio (O/C) by 0.28. A gas chromatography analysis was carried out during this operation and found that an oxygen concentration in the reactor outlet gas was 0 vol % and a propylene conversion rate was 91%.

(3) Reduction Posttreatment

After 75 minutes elapsed from the operation, the oxygen/propylene molar ratio was increased by 0.28 returning to the level before the reduction treatment. After lowering the temperature to 430° C., the gas conditions; the molar ratio of ammonia/propylene, the molar ratio of oxygen/propylene, and the contact time were set so that a sulfuric acid consumption rate defined by the above formula was 20±2 kg/T-AN, an oxygen concentration in the reactor outlet gas was 0.05±0.01 vol %, and a propylene conversion rate was 99.3±0.2%.

After 90 minutes elapsed from setting the gas conditions as described above, the gas condition of the molar ratio of oxygen/propylene was set so that an oxygen concentration in the reactor outlet gas was 1.0±0.1 vol %. After 10 minutes elapsed from setting the gas condition as described above, the molar ratio of oxygen/propylene was set so that an oxygen concentration in the reactor outlet gas was 0.2±0.02 vol %, and after 20 minutes elapsed, the all of the gas supplies were stopped to obtain the catalyst.

The surface nickel concentration/bulk nickel concentration ratio, which was calculated from the surface nickel concentration obtained by measuring SEM/EDX of the obtained catalyst and the bulk concentration of the nickel obtained from the feed composition, was 0.83.

Example 2

A catalyst was obtained by the same operation as Example 1, except that the decrease of the oxygen/propylene molar ratio in the above (2) Reduction treatment was 0.25 and a propylene conversion rate was 96%.

Example 3

A catalyst was obtained by the same operation as Example 1, except that the decrease of the oxygen/propylene molar ratio in the above (2) Reduction treatment was 0.36 and a propylene conversion rate was 89%.

Example 4

A catalyst was obtained by the same operation as Example 1, except that the mixing ratio of ammonium paramolybdate in the above (1) Reduction pretreatment was 0.2 and a propylene conversion rate was 92%.

Example 5

A catalyst was obtained by the same operation as Example 1, except that ammonium paramolybdate in the above (1) Reduction pretreatment was not mixed and a propylene conversion rate was 92%.

Comparative Example 1

A catalyst was obtained by the same operation as Example 1, except that the above (Reduction treatment) was not carried out.

Comparative Example 2

A catalyst was obtained by the same operation as Example 1, except that the decrease of the oxygen/propylene molar ratio in the above (2) Reduction treatment was 0.53 and a propylene conversion rate was 85%.

Example 6

A catalyst was obtained by the same operation as Example 1, except that 60 mass % of a metal oxide, which was produced by adjusting feed masses of the starting materials in such a way that the composition thereof was $Mo_{12}Bi_{0.35}Fe_{1.61}Ni_{3.60}Co_{3.90}Ce_{0.84}Rb_{0.14}O_g$, was used, and the decrease of the oxygen/propylene molar ratio in the above (2) Reduction treatment was 0.29 and a propylene conversion rate was 93%.

Example 7

A catalyst was obtained by the same operation as Example 6, except that the decrease of the oxygen/propylene molar ratio in the above (2) Reduction treatment was 0.23 and a propylene conversion rate was 96%.

Example 8

A catalyst was obtained by the same operation as Example 6, except that the decrease of the oxygen/propylene molar ratio in the above (2) Reduction treatment was 0.38 and a propylene conversion rate was 89%.

Comparative Example 3

A catalyst was obtained by the same operation as Example 6, except that the above (Reduction treatment) was not carried out.

Example 9

A catalyst was obtained by the same operation as Example 1, except that 60 mass % of a metal oxide, which was produced by adjusting feed masses of the starting materials in such a way that the composition thereof was $Mo_{12}Bi_{0.39}Fe_{1.31}Ni_{3.10}Co_{4.05}Ce_{0.87}Rb_{0.10}K_{0.08}O_g$, was used, and the decrease of the oxygen/propylene molar ratio in the above (2) Reduction treatment was 0.27 and a propylene conversion rate was 93%.

Comparative Example 4

A catalyst was obtained by the same operation as Example 9, except that the above (Reduction treatment) was not carried out.

Example 10

A catalyst was obtained by the same operation as Example 1, except that 60 mass % of a metal oxide, which was produced by adjusting feed masses of the starting materials in such a way that the composition thereof was $Mo_{12}Bi_{0.39}Fe_{1.60}Ni_{6.97}Mg_{0.77}Ce_{0.63}Rb_{0.17}O_g$, was used, and the decrease of the oxygen/propylene molar ratio in the above (2) Reduction treatment was 0.32 and a propylene conversion rate was 91%.

Comparative Example 5

A catalyst was obtained by the same operation as Example 10, except that the above (Reduction treatment) was not carried out.

Example 11

A catalyst was obtained by the same operation as Example 1, except that 60 mass % of a metal oxide, which was produced by adjusting feed masses of the starting materials in such a way that the composition thereof was $Mo_{12}Bi_{0.57}Fe_{1.01}Ni_{0.98}Co_{6.83}Mg_{0.98}Ce_{0.38}Rb_{0.12}O_g$, was used, and the decrease of the oxygen/propylene molar ratio in the above (2) Reduction treatment was 0.29 and a propylene conversion rate was 92%.

Comparative Example 6

A catalyst was obtained by the same operation as Example 11, except that the above (Reduction treatment) was not carried out.

Example 12

A catalyst was obtained by the same operation as Example 1, except that 60 mass % of a metal oxide, which was produced by adjusting feed masses of the starting materials in such a way that the composition thereof was $Mo_{12}Bi_{0.27}Fe_{0.95}Ni_{2.95}Co_{6.69}Ce_{0.18}Rb_{0.13}O_g$, was used, and the decrease of the oxygen/propylene molar ratio in the above (2) Reduction treatment was 0.35 and a propylene conversion rate was 90%.

Comparative Example 7

A catalyst was obtained by the same operation as Example 12, except that the above (Reduction treatment) was not carried out.

Example 13

A catalyst was obtained by the same operation as Example 1, except that 60 mass % of a metal oxide, which was produced by adjusting feed masses of the starting materials in such a way that the composition thereof was $Mo_{12}Bi_{0.27}Fe_{0.95}Ni_{1.48}Co_{8.16}Ce_{0.18}Rb_{0.13}O_g$, was used, and the decrease of the oxygen/propylene molar ratio in the above (2) Reduction treatment was 0.24 and a propylene conversion rate was 94%.

Comparative Example 8

A catalyst was obtained by the same operation as Example 13, except that the above (Reduction treatment) was not carried out.

Example 14

A catalyst was obtained by the same operation as Example 1, except that 60 mass % of a metal oxide, which was produced by adjusting feed masses of the starting materials in such a way that the composition thereof was $Mo_{12}Bi_{1.20}Fe_{0.60}Ni_{7.80}Cr_{1.20}K_{0.48}O_g$, was used, and a propylene conversion rate was 92%.

Comparative Example 9

A catalyst was obtained by the same operation as Example 14, except that the above (Reduction treatment) was not carried out.

Example 15

An oxide catalyst in which an oxide having the composition represented by $Mo_{12}Bi_{0.45}Ce_{0.90}Co_{3.00}Fe_{1.70}K_{0.09}Ni_{2.00}Mg_{2.00}Rb_{0.04}O_g$ was supported on 50 mass % of silica with respect to the total catalyst amount was prepared as follows.

A solution obtained by dissolving 43.1 g of bismuth nitrate [$Bi(NO_3)_3 \cdot 5H_2O$], 76.2 g of cerium nitrate [$Ce(NO_3)_3 \cdot 6H_2O$], 133.9 g of iron nitrate [$Fe(NO_3)_3 \cdot 9H_2O$], 114.6 g of nickel nitrate [$Ni(NO_3)_2 \cdot 6H_2O$], 171.8 g of cobalt nitrate [$Co(NO_3)_2 \cdot 6H_2O$], 101.4 g of magnesium nitrate [$Mg(NO_3)_2 \cdot 6H_2O$], 1.77 g of potassium nitrate [$KNO_3$] and 1.15 g of rubidium nitrate [$RbNO_3$] in 395.1 g of a nitric acid aqueous solution having a 16.6 mass % concentration was added to a mixture of 833.3 g of an aqueous silica sol containing 30 mass % of $SiO_2$ having an average particle size of primary particles of 12 nm and 833.3 g of an aqueous silica sol containing 30 mass % of $SiO_2$ having an average particle size of primary particles of 41 nm. A solution in which 413.8 g of ammonium paramolybdate [$(NH_4)_6Mo_7O_{24} \cdot 4H_2O$] was dissolved in 738.7 g of water was added thereto, mixed and stirred to obtain a precursor slurry. Subsequently, the obtained precursor slurry was spray dried using a centrifugal sprayer equipped with a disc rotor installed at the center of the upper part of a dryer. The precursor slurry was spray dried while retaining an inlet air temperature of 240° C. and an outlet temperature of 140° C. of the dryer. The thus obtained dried particles were moved to a kiln and calcined in an air atmosphere. Specifically, a temperature was first increased from room temperature to 320° C. over a period of 2 hours and preliminarily calcination was carried out while the temperature was retained at 320° C. for 2 hours to thereby obtain preliminarily calcined particles. Continuously, the temperature was increased to 580° C. over a period of 3 hours, and the preliminarily calcined particles were finally calcined at 580° C. for 2 hours to thereby obtain an oxide catalyst. A catalyst was obtained by the same operation as Example 1, except that the decrease of the oxygen/propylene molar ratio in the above (2) Reduction treatment was 0.31 and the propylene conversion rate was 92% in the obtained oxide catalyst.

Comparative Example 10

An oxide catalyst in which an oxide having the composition represented by $Mo_{12}Bi_{0.45}Ce_{0.90}Co_{3.00}Fe_{1.70}K_{0.09}Ni_{2.00}Mg_{2.00}Rb_{0.04}O_g$ was supported on 50 mass % of silica with respect to the total catalyst amount was prepared as follows.

A solution obtained by dissolving 43.1 g of bismuth nitrate [$Bi(NO_3)_3 \cdot 5H_2O$], 76.2 g of cerium nitrate [$Ce(NO_3)_3 \cdot 6H_2O$], 133.9 g of iron nitrate [$Fe(NO_3)_3 \cdot 9H_2O$], 114.6 g of nickel nitrate [$Ni(NO_3)_2 \cdot 6H_2O$], 171.8 g of cobalt nitrate [$Co(NO_3)_2 \cdot 6H_2O$], 101.4 g of magnesium nitrate [$Mg(NO_3)_2 \cdot 6H_2O$], 1.77 g of potassium nitrate [$KNO_3$] and 1.15 g of rubidium nitrate [$RbNO_3$] in 395.1 g of a nitric acid aqueous solution having a 16.6 mass % concentration was added to a mixture of 833.3 g of an aqueous silica sol containing 30 mass % of $SiO_2$ having an average particle size of primary particles of 12 nm and 833.3 g of an aqueous silica sol containing 30 mass % of $SiO_2$ having an average particle size of primary particles of 41 nm. A solution in which 413.8 g of ammonium paramolybdate [$(NH_4)_6Mo_7O_{24} \cdot 4H_2O$] was dissolved in 738.7 g of water was added thereto, mixed and stirred to obtain a precursor slurry. Subsequently, the obtained precursor slurry was spray dried using a centrifugal sprayer equipped with a disc rotor installed at the center of the upper part of a dryer. The precursor slurry was spray dried while retaining an inlet air temperature of 240° C. and an outlet temperature of 140° C. of the dryer. The thus obtained dried particles were moved to a kiln and calcined in an air atmosphere. Specifically, a temperature was first increased from room temperature to 320° C. over a period of 2 hours and preliminarily calcination was carried out while the temperature was retained at 320° C. for 2 hours to thereby obtain preliminarily calcined particles. Continuously, the temperature was increased to 580° C. over a period of 3 hours, and the preliminarily calcined particles were finally calcined at 580° C. for 2 hours to thereby obtain an oxide catalyst.

TABLE 1

| | Composition | Surface Ni Concentration/ Bulk Ni Concentration ratio | Surface Ni Concentration/ Surface Mo Concentration ratio | Surface Co Concentration/ Bulk Co Concentration ratio | Surface Co Concentration/ Surface Mo Concentration ratio | Propylene conversion rate [%] | Mo raw material mixing ratio | AN Yield [%] | HCN Yield [%] | AN + HCN (mol) [%] per feed propylene (mol) |
|---|---|---|---|---|---|---|---|---|---|---|
| Example 1 | $Mo_{12}Bi_{0.40}Fe_{1.70}Ni_{5.30}Mg_{2.10}Ce_{0.80}Rb_{0.11}O_g$ | 0.83 | 0.21 | — | — | 91 | 0.4 | 81.9 | 4.1 | 94.2 |
| Example 2 | | 0.67 | 0.18 | — | — | 96 | 0.4 | 81.9 | 3.8 | 93.3 |
| Example 3 | | 1.12 | 0.32 | — | — | 89 | 0.4 | 81.7 | 4.2 | 94.3 |
| Example 4 | | 0.85 | 0.33 | — | — | 92 | 0.2 | 81.7 | 4.1 | 94.0 |
| Example 5 | | 0.81 | 0.36 | — | — | 92 | — | 81.3 | 4.1 | 93.6 |
| Comparative Example 1 | | 0.41 | 0.12 | — | — | — | — | 83.3 | 3.3 | 93.2 |
| Comparative Example 2 | | 1.30 | 0.35 | — | — | 85 | 0.4 | 80.5 | 4.1 | 92.8 |
| Example 6 | $Mo_{12}Bi_{0.35}Fe_{1.61}Ni_{3.60}Co_{3.90}Ce_{0.84}Rb_{0.14}O_g$ | 0.90 | 0.19 | 0.95 | 0.24 | 93 | 0.4 | 83.4 | 3.8 | 94.8 |
| Example 7 | | 0.72 | 0.16 | 0.85 | 0.21 | 96 | 0.4 | 83.5 | 3.5 | 94.0 |
| Example 8 | | 1.05 | 0.36 | 1.25 | 0.32 | 89 | 0.4 | 83.2 | 3.8 | 94.6 |
| Comparative Example 3 | | 0.51 | 0.09 | 0.65 | 0.13 | — | — | 84.5 | 3.1 | 93.8 |
| Example 9 | $Mo_{12}Bi_{0.50}Fe_{1.31}Ni_{3.10}Co_{4.05}Ce_{0.87}Rb_{0.10}K_{0.08}O_g$ | 0.90 | 0.19 | 1.01 | 0.22 | 93 | 0.4 | 83.5 | 3.8 | 94.9 |
| Comparative Example 4 | | 0.44 | 0.13 | 0.65 | 0.16 | — | — | 84.5 | 2.9 | 93.2 |

TABLE 2

|  | Mo | Surface Ni Concentration/ Bulk Ni Concentration ratio | Surface Ni Concentration/ Surface Mo Concentration ratio | Surface Co Concentration/ Bulk Co Concentration ratio | Surface Co Concentration/ Surface Mo Concentration ratio |
|---|---|---|---|---|---|
| Example 10 | $Mo_{12}Bi_{0.39}Fe_{1.60}Ni_{6.97}Mg_{0.77}Ce_{0.63}Rb_{0.17}O_g$ | 0.88 | 0.25 | — | — |
| Comparative Example 5 | | 0.49 | 0.10 | — | — |
| Example 11 | $Mo_{12}Bi_{0.57}Fe_{1.01}Ni_{0.98}Co_{6.83}Mg_{0.98}Ce_{0.38}Rb_{0.12}O_g$ | 0.99 | 0.16 | 1.18 | 0.28 |
| Comparative Example 6 | | 0.50 | 0.08 | 0.75 | 0.12 |
| Example 12 | $Mo_{12}Bi_{0.27}Fe_{0.95}Ni_{2.95}Co_{6.69}Ce_{0.18}Rb_{0.13}O_g$ | 0.92 | 0.20 | 1.07 | 0.24 |
| Comparative Example 7 | | 0.48 | 0.07 | 0.10 | 0.13 |
| Example 13 | $Mo_{12}Bi_{0.27}Fe_{0.95}Ni_{1.48}Co_{8.16}Ce_{0.18}Rb_{0.13}O_g$ | 1.00 | 0.20 | 0.91 | 0.21 |
| Comparative Example 8 | | 0.52 | 0.09 | 0.75 | 0.11 |
| Example 14 | $Mo_{12}Bi_{1.20}Fe_{0.60}Ni_{7.80}Cr_{1.20}Rb_{0.04}O_g$ | 0.74 | 0.25 | — | — |
| Comparative Example 9 | | 0.34 | 0.17 | — | — |
| Example 15 | $Mo_{12}Bi_{0.45}Ce_{0.90}Co_{3.00}Fe_{1.70}K_{0.09}Ni_{2.00}Mg_{2.00}Rb_{0.04}O_g$ | 0.77 | 0.23 | 0.85 | 0.26 |
| Comparative Example 10 | | 0.40 | 0.12 | 0.62 | 0.10 |

|  | Propylene conversion rate [%] | Mo raw material mixing ratio | AN Yield [%] | HCN Yield [%] | AN + HCN (mol) [%] per feed propylene (mol) |
|---|---|---|---|---|---|
| Example 10 | 91 | 0.4 | 83.3 | 3.6 | 94.1 |
| Comparative Example 5 | — | — | 84.4 | 2.8 | 92.8 |
| Example 11 | 92 | 0.4 | 83.6 | 3.7 | 94.7 |
| Comparative Example 6 | — | — | 84.5 | 2.4 | 91.7 |
| Example 12 | 90 | 0.4 | 83.2 | 3.5 | 93.7 |
| Comparative Example 7 | — | — | 84.4 | 2.5 | 91.9 |
| Example 13 | 94 | 0.4 | 82.9 | 3.6 | 93.7 |
| Comparative Example 8 | — | — | 84.1 | 2.6 | 91.9 |
| Example 14 | 92 | 0.4 | 83.0 | 3.2 | 92.6 |
| Comparative Example 9 | — | — | 84.2 | 2.1 | 90.5 |
| Example 15 | 92 | 0.4 | 81.1 | 4.2 | 93.7 |
| Comparative Example 10 | — | — | 81.9 | 3.4 | 92.1 |

INDUSTRIAL APPLICABILITY

The catalyst of the present invention has industrial potency to be used in the production of acrylonitrile and hydrogen cyanide including a step of ammoxidating propylene.

The invention claimed is:

1. A catalyst comprising molybdenum, bismuth, iron, and nickel,
wherein a proportion of a surface concentration of the nickel to a bulk concentration of the nickel is 0.60 to 1.20 and the catalyst has a specific surface area of 10 to 70 m$^2$/g.

2. The catalyst according to claim 1, wherein a proportion of the surface concentration of the nickel to a surface concentration of the molybdenum is 0.15 to 0.40.

3. The catalyst according to claim 1, further comprising cobalt,
wherein a proportion of a surface concentration of the cobalt to a bulk concentration of the cobalt is 0.80 to 1.40.

4. The catalyst according to claim 1, further comprising cobalt,
wherein a proportion of a surface concentration of the cobalt to a surface concentration of the molybdenum is 0.15 to 0.40.

5. The catalyst according to claim 1, wherein a proportion of particles having a particle size of 45 μm or less in a volume-based particle size distribution is 5 to 45%.

6. The catalyst according to claim 1, having a median diameter of 10 to 180 μm.

7. The catalyst according to claim 1, having an apparent specific gravity of 0.8 to 1.2 g/cc.

8. The catalyst according to claim 1, comprising a metal oxide having a composition represented by the following formula (1):

$$Mo_{12}Bi_aFe_bNi_cX_dY_eZ_fO_g \qquad (1)$$

wherein,
X represents one or more elements selected from the group consisting of cobalt, magnesium, calcium, zinc, strontium, barium, and tungsten,
Y represents one or more elements selected from the group consisting of cerium, chromium, lanthanum, neodymium, yttrium, praseodymium, samarium, aluminum, boron, gallium, and indium, Z represents one or more elements selected from the group consisting of sodium, potassium, rubidium, and cesium, a, b, c, d, e, and f satisfy $0.1 \leq a \leq 2.0$, $0.1 \leq b \leq 3.0$, $0.1 \leq c \leq 10.0$, $0 \leq d \leq 10.0$, $0.1 \leq e \leq 3.0$, and $0.01 \leq f \leq 2.0$, respectively, and g is number of oxygen atoms required to satisfy valence requirements of other elements present.

9. The catalyst according to claim 1, further comprising a silica-containing carrier.

10. The catalyst according to claim 1 for use in ammoxidation.

11. A method for producing the catalyst according to claim 1, comprising:

a step of spray drying a slurry containing molybdenum, bismuth, iron, and nickel to obtain dried particles, and calcining the dried particles in air to obtain calcined particles, and a step of reducing the calcined particles in the presence of a reducing gas and oxygen to obtain said catalyst.

12. The method for producing the catalyst according to claim 11, wherein molybdenum is further added in the step of reduction in the presence of a reducing gas and oxygen.

13. A method for producing acrylonitrile, comprising a step of reacting propylene, molecular oxygen, and ammonia in the presence of the catalyst according to claim 1.

14. A catalyst comprising molybdenum, bismuth, iron, and nickel, wherein a proportion of a surface concentration of the nickel to a bulk concentration of the nickel is 0.60 to 1.20, and a proportion of the surface concentration of the nickel to a surface concentration of the molybdenum is 0.15 to 0.40.

15. The catalyst according to claim 14, further comprising cobalt, wherein a proportion of a surface concentration of the cobalt to a bulk concentration of the cobalt is 0.80 to 1.40.

16. The catalyst according to claim 14, further comprising cobalt, wherein a proportion of a surface concentration of the cobalt to a surface concentration of the molybdenum is 0.15 to 0.40.

17. A catalyst comprising molybdenum, bismuth, iron, and nickel, wherein a proportion of a surface concentration of the nickel to a bulk concentration of the nickel is 0.60 to 1.20, and a proportion of particles having a particle size of 45 μm or less in a volume-based particle size distribution is 5 to 45%.

* * * * *